(12) United States Patent
La Fontaine et al.

(10) Patent No.: US 6,608,321 B1
(45) Date of Patent: Aug. 19, 2003

(54) DIFFERENTIAL WAVELENGTH INSPECTION SYSTEM

(75) Inventors: Bruno M. La Fontaine, Pleasanton, CA (US); Harry J. Levinson, Saratoga, CA (US); Jeffrey A. Schefske, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 169 days.

(21) Appl. No.: 09/773,968

(22) Filed: Feb. 1, 2001

(51) Int. Cl.[7] .................. G01N 21/00; G01N 21/64; G01N 21/88; G01B 11/06
(52) U.S. Cl. .............. 250/559.44; 250/559.4; 250/559.41; 250/559.42; 250/559.43; 250/559.45; 356/237.1; 356/237.2; 356/237.3; 356/237.4; 356/237.5
(58) Field of Search ............... 250/250, 559.2, 250/559.39, 559.4, 559.44; 356/237.1, 237.2, 237.3–237.5

(56) References Cited

U.S. PATENT DOCUMENTS

| | | | | |
|---|---|---|---|---|
| 4,128,142 A | * | 12/1978 | Satoh et al. ............... 187/293 |
| 4,392,120 A | * | 7/1983 | Mita et al. ................. 382/199 |
| 4,547,895 A | * | 10/1985 | Mita et al. ................. 382/144 |
| 4,595,289 A | * | 6/1986 | Feldman et al. ......... 356/237.5 |
| 4,795,260 A | * | 1/1989 | Schuur et al. ............. 356/400 |
| 4,943,734 A | * | 7/1990 | Johnson et al. ........ 250/559.18 |
| 5,023,714 A | | 6/1991 | Lemelson |
| 5,278,012 A | | 1/1994 | Yamanaka et al. |
| 5,384,230 A | * | 1/1995 | Berg ......................... 430/313 |
| 5,486,919 A | * | 1/1996 | Tsuji et al. ................. 356/484 |
| 6,002,740 A | * | 12/1999 | Cerrina et al. ............... 378/43 |
| 6,014,209 A | | 1/2000 | Bishop |
| 6,091,488 A | | 7/2000 | Bishop |
| 6,208,421 B1 | | 3/2001 | Maris et al. |
| 2001/0052975 A1 | * | 12/2001 | Biellak et al. ........... 356/237.3 |
| 2002/0027663 A1 | * | 3/2002 | Mueller-Rentz ............. 356/614 |
| 2002/0034198 A1 | * | 3/2002 | Masuda ......................... 372/5 |
| 2002/0088952 A1 | * | 7/2002 | Rao et al. ............... 250/559.45 |

* cited by examiner

*Primary Examiner*—John R. Lee
*Assistant Examiner*—Bernard Souw
(74) *Attorney, Agent, or Firm*—Foley & Lardner

(57) ABSTRACT

An inspection tool or inspection system can be utilized to determine whether the appropriate pattern is on a reticle. The reticle can be associated with EUV lithographic tools. The system utilizes at least two wavelengths of light. The light is directed to the reticle at the at least two wavelengths of light and detected by a detector. The image associated with the first wavelength is subtracted from or otherwise processed with respect to the image associated with the second wavelength to improve contrast ratio.

20 Claims, 6 Drawing Sheets

DIFFERENTIAL WAVELENGTH INSPECTION SYSTEM

CROSS REFERENCE TO RELATED APPLICATIONS

The present application is related to U.S. patent application Ser. No. 09/774,000, entitled "An Inspection System with Contrast Enhancement" filed on an even date herewith by La Fontaine and assigned to the assignee of the present application.

FIELD OF THE INVENTION

The present invention relates generally to an inspection system and an inspection method. More particularly, the present invention relates to an inspection system for and a method of inspecting a pattern on a reticle or photo mask for defects and errors.

BACKGROUND OF THE INVENTION

Semiconductor fabrication techniques often utilize a mask or reticle. Radiation is provided through or reflected off the mask or reticle to form an image on a semiconductor wafer. The wafer is positioned to receive the radiation transmitted through or reflected off the mask or reticle. The image on the wafer corresponds to the pattern on the mask or reticle. The radiation can be light, such as ultraviolet light, vacuum ultraviolet (VUV) light, extreme ultraviolet light (EUV) and deep ultraviolet light. The radiation can also be x-ray radiation, e-beam radiation, etc.

One advanced form of lithography is extreme ultraviolet (EUV) light lithography. A conventional EUV system (e.g., an optical reduction camera or stepper) utilizes an EUV radiation source, a first EUV lens assembly (e.g., a condenser lens), an EUV reticle, and a second EUV lens assembly (e.g., an objective lens). EUV radiation can be created at the EUV radiation source and projected onto the EUV reticle. The EUV reticle is typically a resonant-reflective medium including a pattern of absorbing material.

The EUV reticle reflects a substantial portion of the EUV radiation which carries an IC pattern formed on the reticle to the second EUV lens assembly. The first and second lens assemblies can be an all resonant-reflective imaging system including an aspheric optical system at 4:1 demagnification (e.g., a series of high precision mirrors). EUV radiation reflected off the EUV reticle is provided from the second EUV lens assembly to a photoresist coated wafer.

EUV lithography utilizes radiation in a wave length range of 5 to 70 nanometers (e.g., 11–13 nanometers). A conventional EUV reticle can be a multilayer medium including an absorber pattern across its surface. The multilayer medium can utilize molybdenum/silicon (Mo—Si) layers or molybdenum/beryllium layers (Mo—Be). The absorber pattern can be one or more layers of Chromium (Cr) material selectively arranged on a top surface of the multilayer medium.

Tools, such as, masks or reticles, for lithographic IC fabrication processes must be inspected to ensure that the proper pattern is present on the reticle and to ensure that defects are not present on the reticle. Defects can be introduced during the fabrication of the mask or reticle, during handling of the mask or reticle, and during use of the reticle in the EUV lithographic system. Inspections can verify that the mask or reticle has the proper physical characteristics, critical dimensions, and registration.

Inspections ensure that the photoresist material can be selectively formed within specified tolerances. For example, mistakes or unacceptable process variations associated with the mask or reticle should be corrected before any physical changes are produced on the wafer itself, such as, by doping, etching, etc.

Various techniques can be utilized to inspect masks and reticles. For example, optical microscopes, scanning electron microscopes (SEMs) and laser-based systems have been utilized for inspection tasks and line width measurement tasks. Holographic principles have even been used to detect defects on masks and reticles.

The amount of automation in these inspection tasks has varied. For example, human vision may be required in some inspection procedures to determine and classify defects. Other inspection tasks have been automated so that the human operator is completely removed from the defect inspection tasks. Automated mask or reticle inspection systems include the KLARIS system manufactured by KLA the Chipcheck system manufactured by Cambridge Instruments and the 8100 XP-R CD SEM Manufactured by KLA-TEACOR Corp. Defect detection and pattern verification in these automated systems can be accomplished either by mask-to-mask or mask-to-standard comparisons.

One type of conventional automated defect detection system provides radiation or light from a light source to a surface of the mask or reticle being inspected. Light from the light source is directed through an optical system to the mask or reticle. The optical system focuses the light and can include mirrors, lenses, and prisms. The light strikes the surface of the reticle and is reflected. Alternatively, the light can pass through the mask.

The light reflected from the reticle or the light through the mask is sensed by photoelectric detectors. The light can be provided through an optical system including mirrors, lenses, and prisms. Generally, the light is analyzed to determine whether the appropriate image is on the reticle or mask and whether or not defects are present. Defects can include scratches, misalignment, line errors, contamination, dust, etc.

Conventional inspection systems utilizing conventional inspection wavelengths cannot adequately inspect EUV reticles or masks. The contrast between the absorber pattern and the multilayer is poor at conventional inspection wavelengths. The contrast observed with conventional inspection systems is less than fifty percent (50%). The contrast observed with conventional inspections systems has been 50 percent or less. Accordingly, ascertaining the correctness of the image on the EUV reticle as well as determining whether any defects are present on the EUV reticle is difficult with conventional inspection systems.

Thus, there is a need for a highly accurate inspection system that can be utilized to detect defects and patterns on a mask or reticle. Further, there is a need for a semiconductor fabrication inspection tool for detecting defects and patterns on an EUV reticle. Even further still, there is need for a process or method of detecting patterns on an EUV reticle which obtains enhanced contrast and greater inspection functionality capability. Even further still, there is a need for an inspection tool and inspection method that is capable of reliably detecting patterns on an EUV reticle and capable of greater inspection capability.

SUMMARY OF THE INVENTION

An exemplary embodiment relates to an inspection system. The inspection system is used with a reticle including a multilayer and an absorbing pattern. The inspection system includes a light source and a detector. The light source sequentially provides light at a first wavelength and at a second wavelength. The detector is positioned to receive the light after the light is reflected off the reticle.

Another exemplary embodiment relates to a method of inspecting a reticle. The reticle is associated with the manufacture of an integrated circuit. The method includes providing radiation at a first wavelength to the reticle and receiving the radiation at the first wavelength reflected from the reticle. The method also includes providing radiation at a second wavelength to the reticle and receiving the radiation at the second wavelength reflected from the reticle.

Still another exemplary embodiment relates to a inspection system for an EUV reticle for use in an integrated circuit fabrication system. The inspection system includes means for providing radiation at a first wavelength to the reticle, means for providing radiation at a second wavelength to the reticle, and means for detecting the radiation at the first wavelength and the radiation at the second wavelength. The inspection system further includes means for comparing the reflected radiation at the first wavelength to the reflected radiation at the second wavelength.

BRIEF DESCRIPTION OF THE DRAWINGS

The present invention will hereafter be described with reference to the accompanying drawings, wherein like numerals denote like elements, and.

DETAILED DESCRIPTION OF THE PREFERRED EMBODIMENTS

Figure 1:
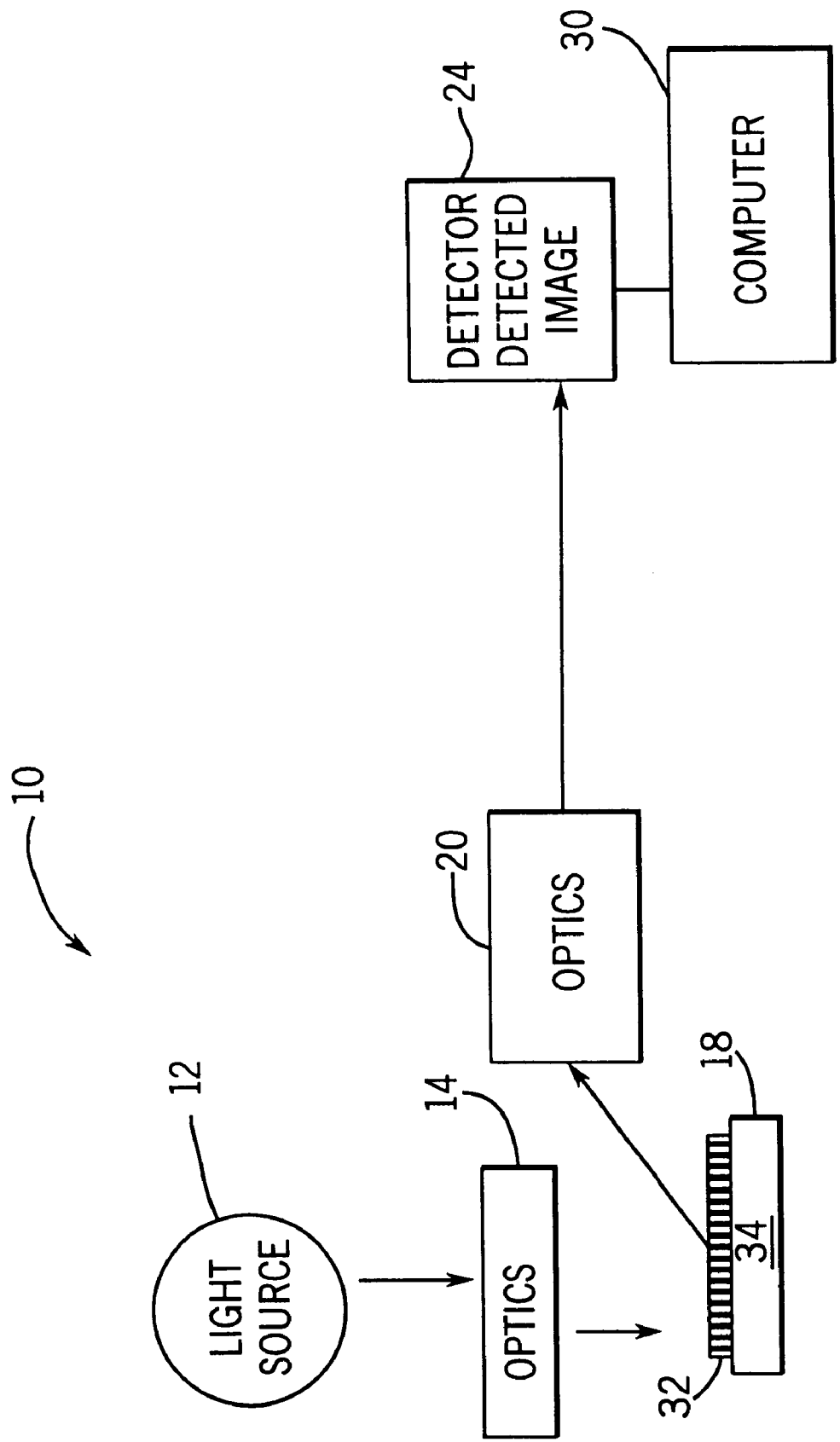
FIG. 1 is a general schematic block diagram of an inspection system for inspecting a mask or reticle in accordance with an exemplary embodiment.

With reference to FIG. 1, an inspection system 10 is configured to analyze the lithographic pattern (e.g., the absorber or reflector pattern) associated with a mask or reticle 18. Mask or reticle 18 can be any tool for use in integrated circuit (IC) lithographic equipment. System 10 advantageously achieves a higher contrast of an advanced lithographic pattern than possible with conventional inspection tools.

System 10 can detect defects or errors associated with reticle 18. For example, system 10 can be utilized to determine if detects manifested in a variety of forms including foreign matter, dust, scratches, bubbles, striations, steps, or other improper structures are provided on reticle 18. In addition, system 10 allows mask or reticle 18 to be inspected to determine that the appropriate absorber pattern or reflective pattern has been provided on reticle 18. System 10 can ensure that critical dimensions on reticle 18 are within tolerances.

Reticle 18 is preferably a lithographic tool for use in extreme ultraviolet (EUV) light lithography, wherein radiation having a wavelength less than 70 nm is utilized (most preferably, wavelengths between 5 and 14 nm). For example, radiation or ultraviolet light at a wavelength of 13 nm can be reflected off reticle 18 to a semiconductor wafer coated with a photoresist. Alternatively, reticle 18 can be employed at other locations with respect to the EUV or advanced lithographic system.

Inspection system 10 includes a light source 12, an optical system 14, an optical system 20, a detector 24, and a computer 30. System 10 is configured to provide radiation through optical system 14, off reticle 18, and to detector 24. Preferably, system 10 can provide automated analysis of reticle 18. Alternatively, system 10 can be utilized to enhance manual visual analysis of reticle 18, such as, through a microscope.

Light source 12 can be any number of sources of electromagnetic radiation. Light source 12 can be a single light source or multiple light sources for providing radiation at two or more wavelengths to reticle 18. Preferably, the light source 12 provides light or radiation at a first wavelength ($\lambda_1$) followed by light or radiation at a second wavelength ($\lambda_2$). Preferably, the first and second wavelengths ($\lambda_1$ and $\lambda_2$) of light provided by light source 12 are different than the wavelength ($\lambda_{EUV}$) of light utilized by the EUV lithographic system. For example, if reticle 18 is designed to be utilized in a EUV lithographic system utilizing radiation at a wavelength ($\lambda_{EUV}$) of 13 nm, light source 12 preferably provides light at wavelengths not equal to 13 nm.

Light source 12 can be a laser light source that emits two wavelengths, such as, an argon laser. Alternatively, light source 12 can be an excimer laser, an ND:YAG laser, a frequency multiplied ND:YAG laser, a He—Ne scanning laser, or other light source. Light source 12 can provide light at any number of wavelengths outside of the EUV wavelength ranges.

Light provided from light source 12 is reflected off reticle 18 in accordance with the pattern on reticle 18, to optical system 20. Optical system 20 provides the reflected light to detector 24 which provides an indication of the image at the first wavelength ($\lambda_1$) and an indication of the image at the second wavelength ($\lambda_2$) to computer 30. Computer 30 analyzes the images to inspect reticle 18 for defects.

Detector 24 can be a laser-light detector, a photo detector, a photo cell or other devices for converting a light signal to an electric signal. Detector 24 can include circuitry for converting the electric signal to a digital word or data. In one embodiment, detector 24 can be a matrix of photo detectors. In addition, detector 24 can be integrated with computer 30. Detector 24 can also be configured to provide the subtraction function.

Computer 30 receives the electric signal from detector 24 and determines whether a pattern 32 on reticle 18 is appropriate by analyzing the difference of the light received by detector 24 at the first and second wavelengths ($\lambda_1$ and $\lambda_2$). For example, computer 30 can compare the difference to a library of images stored in memory or on a database. Computer 30 can be a personal computer (PC), a workstation, a software control device, or other system capable of analyzing signals from detector 24. Advantageously, system 10 is not susceptible to problems associated with low contrast present in conventional systems. Due to the use of at least two wavelengths ($\lambda_1$ and $\lambda_2$), computer 30 maximizes contrast.

Reticle 18 is advantageously designed with materials that have particular reflective characteristics at the first wavelength ($\lambda_1$) and the second wavelength ($\lambda_2$). As described in greater detail with reference to FIG. 4 below, reticle 18 includes a pattern 32 on a substrate 34. Reticle 18 can be a variety of shapes and sizes depending upon circuit requirements and lithographic tool designs.

Pattern 32 has reflective portions and absorptive portions. The materials of reticle 18 are chosen so that either:

(1) the intensity of light reflected off of the absorptive portions is approximately equal at the first and second wavelengths ($\lambda_1$ and $\lambda_2$) and yet the intensity of light reflected off the reflective portions is different at the first wavelength ($\lambda_1$) than at the second wavelength ($\lambda_2$); or (2) the intensity of light reflected off the reflective portions is approximately equal at the first and second wavelengths ($\lambda_1$ and $\lambda_2$), and yet the intensity of light reflected off the absorptive portions is different at the first wavelength ($\lambda_1$) than at the second wavelength ($\lambda_2$).

Accordingly, the intensity (I) of light reflected of reticle 18 can be represented mathematically as follows:

$$I_{at\ \lambda_1,\ ABS} \cong I_{at\ \lambda_2,\ ABS} \text{ and } I_{at\ \lambda_1,\ REFL} \neq I \text{ at } \lambda_{2,\ REFL}; \quad (1)$$

or $$I_{at\ \lambda_1,\ ABS} \neq I_{at\ \lambda_2,\ ABS}; \text{ and } I_{at\ \lambda_1,\ REFL} \cong I_{at\ \lambda_2,\ REFL}. \quad (2)$$

$I_{at\ \lambda_1,\ ABS}$ is the intensity of light at the first wavelength ($\lambda_1$) reflected off absorptive portions of reticle 18. $I_{at\ \lambda_2,\ ABS}$ is the intensity of light at the second wavelength ($\lambda_2$) reflected off absorptive portions of reticle 18. $I_{at\ \lambda_1,\ REFL}$ is the intensity of light at the first wavelength ($\lambda_1$) reflected off the reflective portions of reticle 18. $I_{at\ \lambda_2,\ REFL}$ is the intensity of light at the second wavelength ($\lambda_2$) reflected off the reflective portions of reticle 18.

Computer 30 advantageously subtracts the intensity of light off reticle 18 received at the first wavelength of light ($I_{at\ \lambda_1,\ ABS} + I_{at\ \lambda_2,\ REFL}$) from the intensity of light off reticle 18 received at the second wavelength of light ($I_{at\ \lambda_2,\ ABS} + I_{at\ \lambda_1,\ REFL}$) to obtain a higher contrast ratio. Computer 30 can receive the entire image associated at the first wavelength of light and subtract that entire image from the image received at the second wavelength of light. Alternatively, computer 30 can sequentially subtract the intensity as received at various points or portions of reticle 38.

In yet another alternative embodiment, light source 12 can provide both the first and second wavelengths ($\lambda_1$, and $\lambda_2$) of light simultaneously. In this embodiment, computer 30 through the use of filters or detectors tuned to the appropriate wavelengths can receive the images associated with both wavelengths ($\lambda_1$ and $\lambda_2$) of light simultaneously.

When the images are subtracted, the contrast is enhanced. Contrast is the ratio of light from the reflective portions to light from the absorptive portions. For example, contrast, C, can be mathematically defined as:

$$ABS\left|\frac{\Delta R_{ABS} - \Delta R_{REFL}}{\Delta R_{ABS} + \Delta R_{REFL}}\right|$$

where $\Delta R_{ABS} = I_{at\ \lambda_1,\ ABS} - I_{at\ \lambda_2,\ ABS}$;

and $\Delta R_{REFL} = I_{at\ \lambda_1,\ REFL} - I_{at\ \lambda_2,\ REFL}$.

When the absorptive portions or reflective portions have a reflectance that is the same at the first and second wavelengths, ($\lambda_1$ and $\lambda_2$), $\Delta R_{ABS}$ equals zero and the contrast is maximized (e.g., C equals one). For example, if $\Delta R_{ABS}$ equals zero, the contrast, C, equals the absolute value of $=\Delta RE_{REFL}/\Delta R_{REFL}$ which equals one. The same result is obtained if $\Delta R_{REFL}$ is set to zero and $\Delta R_{ABS}$ is not equal to zero.

Figure 2:
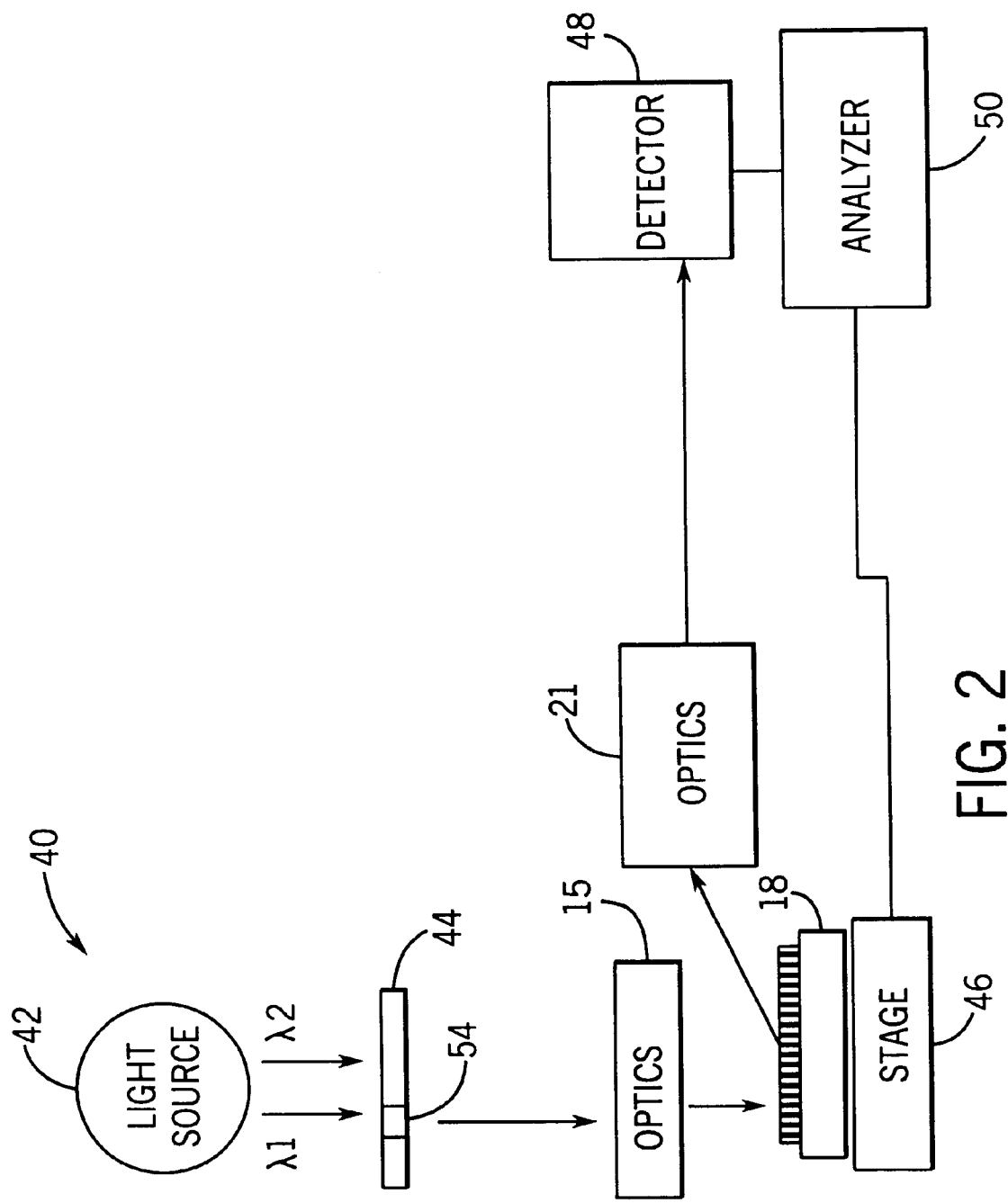
FIG. 2 is a general schematic block diagram of an inspection system, similar to the inspection system illustrated in FIG. 1, the inspection system is for inspecting a reticle in accordance with another exemplary embodiment, the inspection system is shown providing light at a first wavelength ($\lambda_1$) to the reticle.

With reference to FIG. 2, an inspection system 40, similar to inspection system 10, includes a light source 42 similar to light source 12 (FIG. 1), a filter wheel 44, optical system 15 similar to optical system 14 (FIG. 1), and a stage 46. System 40 also includes optical system 21, a detector 48 and an analyzer 50. Optical system 21 is similar to optical system 20 (FIG. 1).

Filter wheel 44 is a device for selectively providing the light at the first wavelength ($\lambda_1$) or at the second wavelength ($\lambda_2$) to optical system 15. Preferably, filter wheel 44 includes portion 54 which only allows light at the first wavelength ($\lambda_1$) to pass. Filter wheel 44 can include optical systems, such as, beam splitters, reflectors, mirrors, or other devices.

Filler wheel 44 can include shutters, switches or other devices for selectively providing light. In alternative embodiments, wheel 44 can be placed at different locations in system 40. Wheel 44 can be controlled by analyzer 50.

Inspection system 40 provides light at the first wavelength ($\lambda_1$) through optical system 15 off reticle 18 through optical system 21 to detector 48. Detector 48 provides an electric signal or data representative of the reflected image at the first wavelength ($\lambda_1$) to analyzer 50, which is similar to computer 30 (FIG. 1). Analyzer 50 can control stage 46 upon which reticle 18 sits. Analyzer 50 can keep track of the positioning of reticle 18 as stage 46 moves reticle 18 with respect to light source 42.

Figure 3:
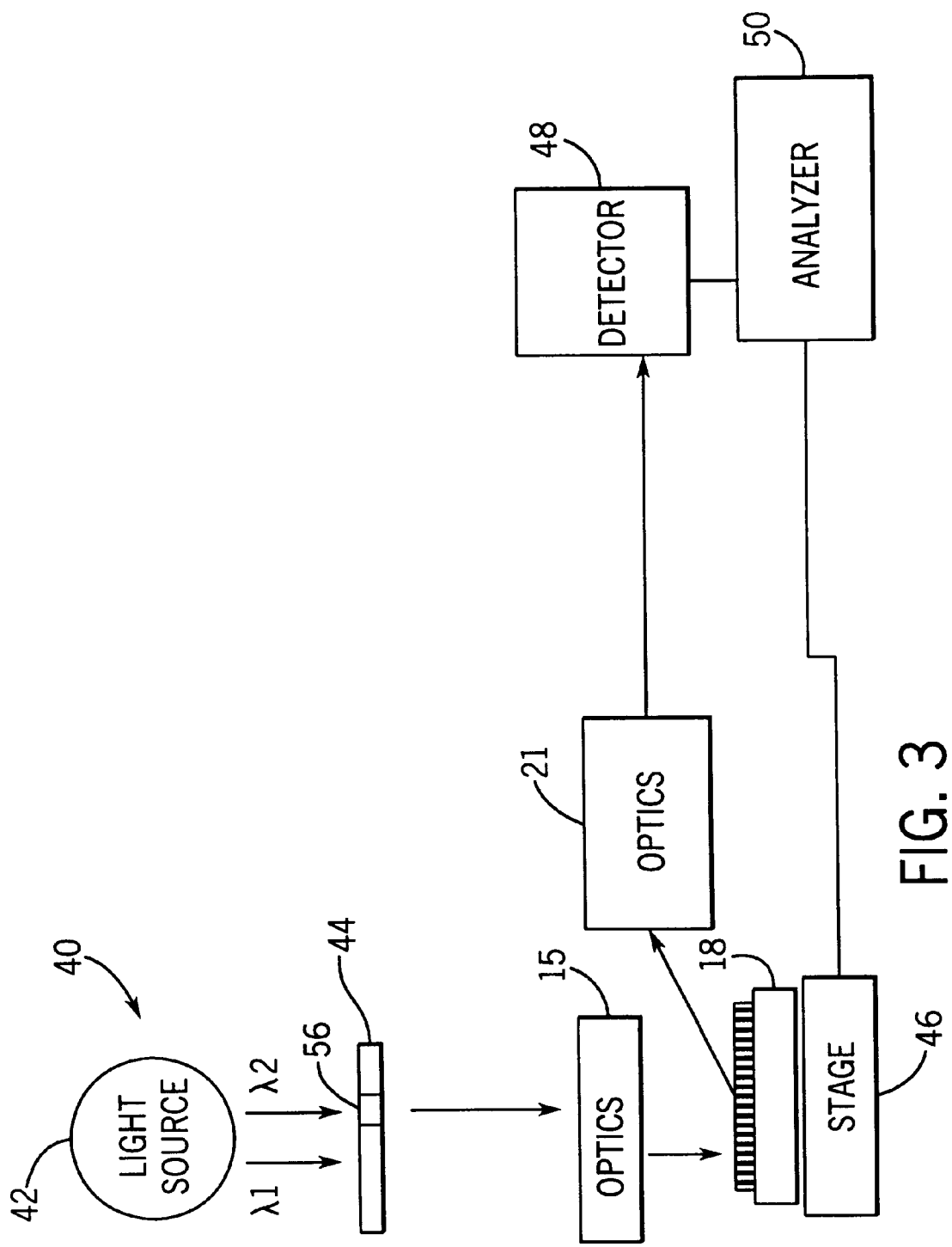
FIG. 3 is a general schematic block diagram of the inspection system illustrated in FIG. 2, the inspection system is shown providing light at a second wavelength ($\lambda_2$) to the reticle in accordance with yet another exemplary embodiment.

With reference to FIG. 3, system 40 is configured to provide light from light source 42 through a second portion 56 of filter wheel 44 which only provides light at the second wavelength ($\lambda_2$) to optical system 15. In this way, light at the second wavelength is provided off reticle 18, through optical system 21 to detector 48. Detector 48 provides an electric signal or data representative of the reflected image at the second wavelength ($\lambda_2$). Thus, filter wheel 44 provides light at the first wavelength ($\lambda_1$) and at the second wavelength ($\lambda_2$) so that analyzer 50 can receive an intensity signal representative of pattern 32 on reticle 18 at the first wavelength and pattern 32 of reticle 18 at the second wavelength.

Figure 4:
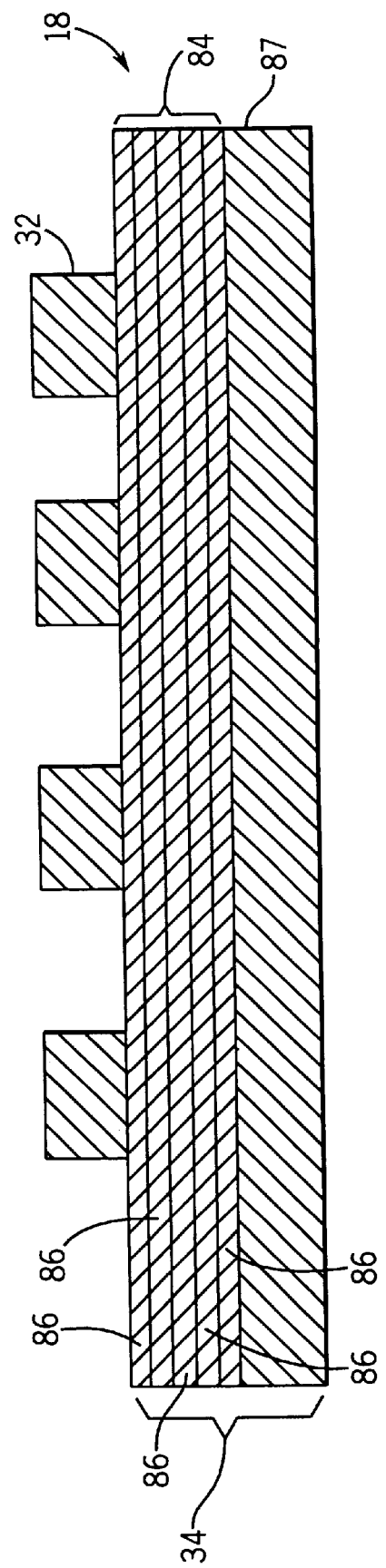
FIG. 4 is a more detailed schematic cross-sectional view of the reticle illustrated in FIGS. 1, 2 and 3.

With reference to FIG. 4, as discussed with reference to FIG. 1, reticle 18 includes a substrate 34 and absorptive material 32. Substrate 34 includes a multilayer 84 comprised of individual layers 86. Substrate 34 can include a low thermal expansion (LTE) base or silicon base 87. The LTE base can be an ultra-low expansion (ULE) glass manufactured by Corning.

Layers 86 of multilayer 84 can be alternating layers of molybdenum/beryllium (Mo—Be) films which are configured for maximum reflectance in the EUV band (e.g., 11–14 nanometer wavelength). Alternatively, layers 20 can be molybdenum/silicon (Mo—Si) layers configured for maximum reflectance in the EUV band.

A pair of layers 86 can be 7 nm thick. Multilayer 84 can include forty pairs of layers 20 and can have a total thickness of 300 nm. Multilayer 84 can be manufactured by Osmic.

Absorptive material 32 can be a metal containing material, such as, chromium, chromium oxide, titanium nitride, tantalum nitride or other reflective material. Material 32 can be 50 nm thick. Absorptive material 32 is selectively formed on multilayer 84 to form a pattern. The selective formation can be accomplished by a lithographic process. Material can be arranged in any pattern utilized to form an IC.

In one embodiment, the EUV absorber pattern 32 has the same reflective characteristics at the first wavelength ($\lambda_1$) as at the second wavelength ($\lambda_2$). In one embodiment, the multilayer material 84 is chosen to have different reflective characteristics at the first wavelength ($\lambda_1$) and at the second wavelength ($\lambda_2$). The first wavelength ($\lambda_1$) can be 633 nm and the second wavelength ($\lambda_2$) can be 365 nm.

In another embodiment, absorptive material 32 is chosen to have different reflective characteristics at the first wavelength than at the second wavelength and multilayer 84 is chosen to have the same reflective characteristics at the first wavelength and the second wavelength.

Figure 5:
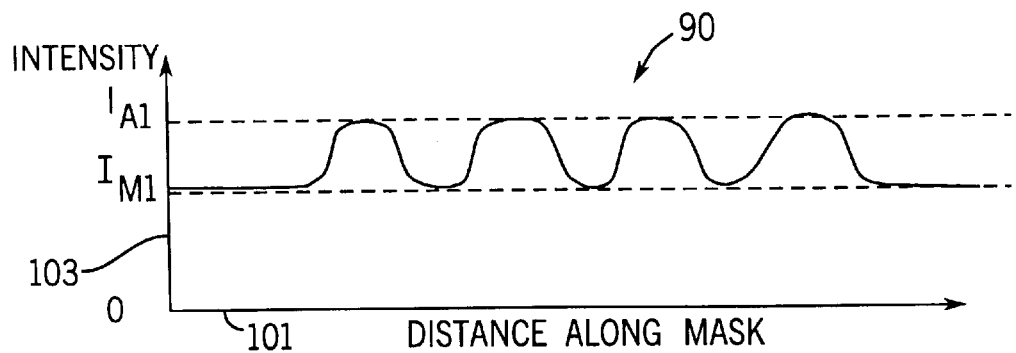
FIG. 5 is a graph showing the intensity of light reflected off a reflective portion and off an absorbing portion of the reticle illustrated in FIG. 4 when light at the first wavelength ($\lambda_1$) is provided to the reticle.
Figure 6:
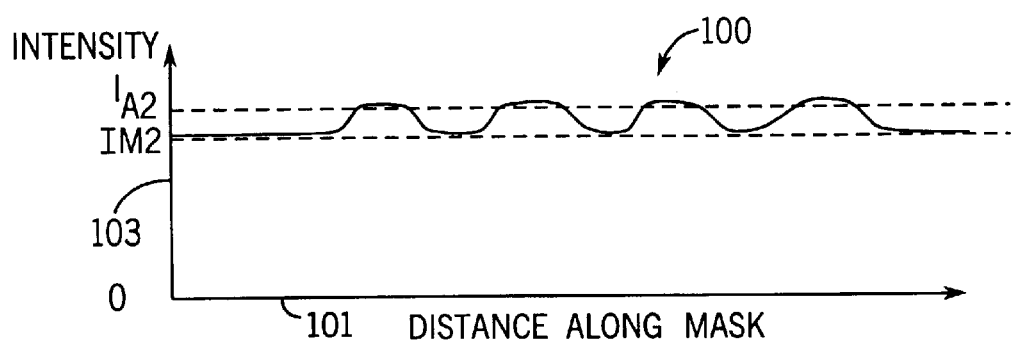
FIG. 6 is a graph showing the intensity of light reflected off a reflective portion and off an absorbing portion of the reticle illustrated in FIG. 4 when light at the second wavelength ($\lambda_2$) is provided to the reticle.

With reference to FIGS. 5 and 6, the image received at detector 48 (FIGS. 2 and 3) is represented by graphs 90 and 100. The x-axis 101 of graphs 90 and 100 represent the position on reticle 38, and y-axis 103 of graphs 90 and 100 represents intensity of light reflected from the reticle 38.

Graph 90 represents the intensity of light at the first wavelength ($\lambda_1$) reflected from the mask of FIG. 4. The maximum intensity $I_{A1}$ comes from the patterned EUV absorber, whereas the multilayer provides a reflected intensity $I_{M1}$. The resulting contrast for this image is $C_1=|I_{A1}-I_{M1}|/(I_{A1}+I_{M1})$, so that if the reflectivity of the multilayer and the absorber are comparable, $I_{A1}$ will be close to $I_{M1}$, and the contrast $C_1$ will be small.

In FIG. 6, graph 100 represents the intensity of light at the second wavelength ($\lambda_2$) reflected from the mask of FIG. 3. The maximum intensity $I_{A2}$ comes from the patterned EUV absorber, whereas the multilayer provides a reflected intensity $I_{M2}$. Again, the resulting contrast for this image is $C_2=|I_{A2}-I_{M2}|/(I_{A2}+I_{M2+})$, so that if the reflectivity of the multilayer and the absorber are also comparable at the second wavelength, $I_{A2}$ will be close to $I_{M2}$, and the contrast $C_2$ will also be small.

Figure 7:
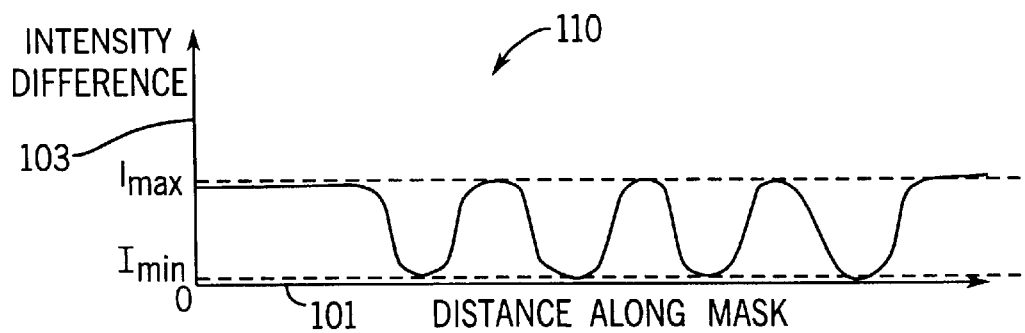
FIG. 7 is a graph showing the difference in the intensity of light at the first wavelength ($\lambda_1$) illustrated in FIG. 5 and the intensity of light at the second wavelength ($\lambda_2$) illustrated in FIG. 6.

With reference to FIG. 7, graph 110 shows an intensity distribution proportional to the difference of intensity obtained at the two wavelengths (FIGS. 5 and 6). Since the reflectivity of the patterned absorber was very similar for both wavelength $\lambda_1$ and $\lambda_2$, the intensity $I_{min}$ of FIG. 7 is very close to zero, while $I_{max}$ is many times larger. In one embodiment where Cr is used as an absorber pattern over a Mo/Si multilayer, a contrast of about 70% can be achieved in this way.

Figure 8:
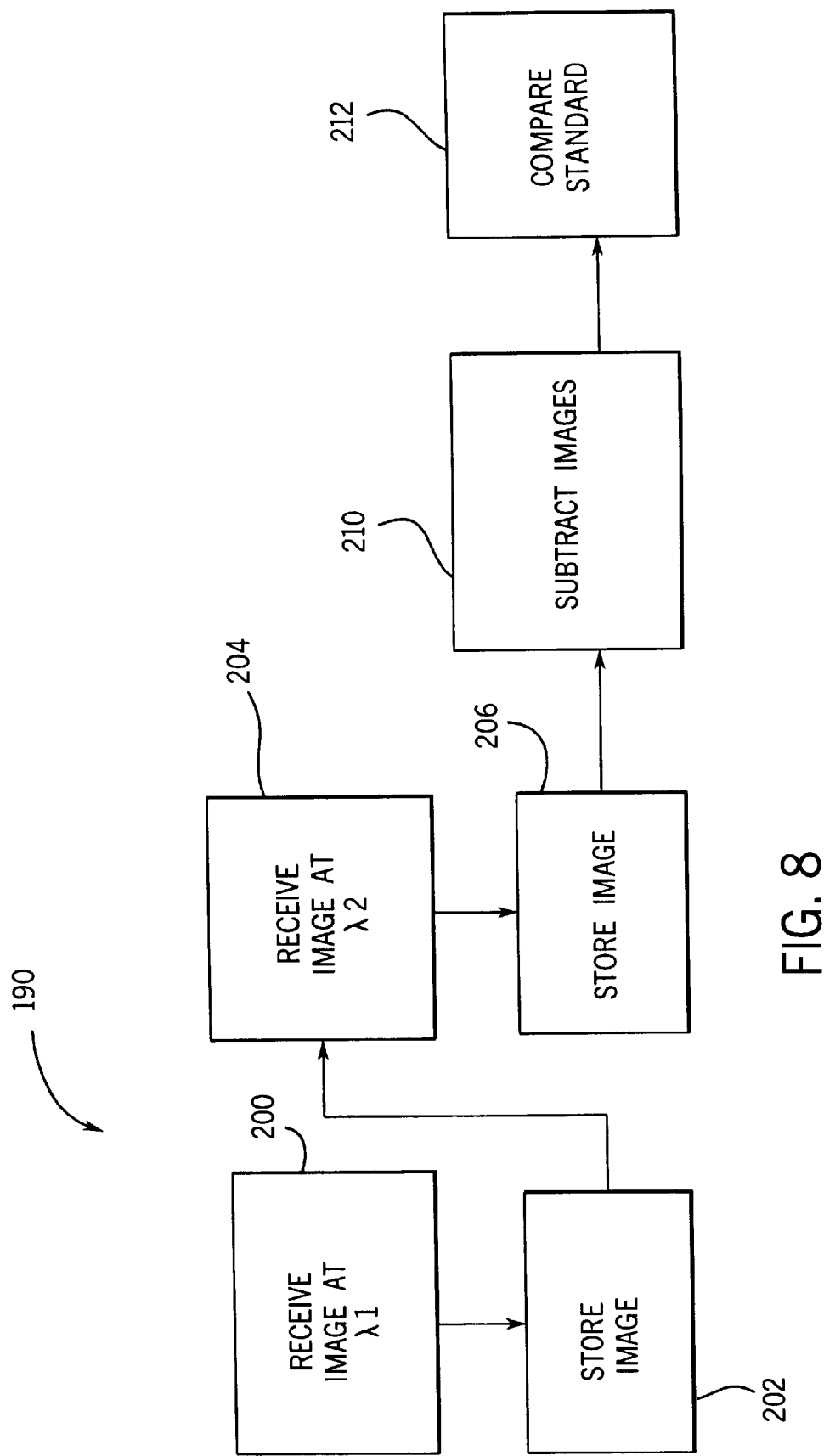
FIG. 8 is a flow diagram showing the operation of the inspection systems illustrated in FIGS. 1–3 in accordance with still another exemplary embodiment.

With reference to FIG. 8, the operation of system 40 is described with reference to FIGS. 3–7 according to a flow diagram 190. At a step 200, system 40 receives light at the first wavelength ($\lambda_1$) at detector 48. Detector 48 provides an electrical indication of the image on reticle 18 (e.g., graph 90). The image from detector 48 is stored at a step 202 by analyzer 50.

At a step 204, light source 42 provides light at the second wavelength ($\lambda_2$) through portion 56 of filter wheel 44 to provide light at the second wavelength ($\lambda_2$) to reticle 18. The image at the second wavelength is received by detector 48 (e.g., graph 100).

At a step 206, the image received from detector 48 representative of the image at the second wavelength ($\lambda_2$) is stored. At a step 210, analyzer 50 subtracts the image stored at step 202 from the image stored at step 206 to achieve higher contrast (e.g., graph 110). At a step 212, analyzer 50 compares the subtracted images to a standard image.

The standard image is associated with the acceptable specification tolerances for reticle 18. The standard image can be based upon an actual reticle which is known to function properly, based upon a prediction of what a working reticle should look like, or other design parameters. Analyzer 50 can also compare the signal to libraries of images to determine what types of errors are included on reticle 38. These errors can be classified and located. In an alternative embodiment, the subtracted images of step 210 can be viewed on a display screen.

It is understood that while preferred embodiment and specific examples are given, they are for the purpose of illustration only and is not limited to the precise details disclosed. For example, although specific wavelengths of light are described, other types of light can be utilized. Further, although two wavelengths are discussed, different wavelengths and more than two wavelengths can be utilized. Various modifications may be made in the details within the scope and range of the equivalence of the claims without departing from what is claimed.

What is claimed is:

1. An inspection system for a reticle including a multilayer and an absorbing pattern, the inspection system comprising:
   a light source; and
   a detector, wherein the light source sequentially provides light at a first wavelength and at a second wavelength, wherein the detector is positioned to receive the light at the first wavelength and the light at the second wavelength after the light is reflected off the reticle, wherein the absorbing pattern has similar reflective characteristics at the first and second wavelengths and the multilayer portion has different reflective characteristics at the first and second wavelengths or wherein the absorbing pattern has different reflective characteristics at the first and second wavelengths and the multilayer portion has similar reflective characteristics at the first and second wavelength, whereby the light at the first and second wavelengths is processed to increase contrast ratio.

2. The inspection system of claim 1, further comprising an analyzer coupled to the detector, the analyzer subtracting the light received at the first wavelength from the light received at the second wavelength.

3. The inspection system of claim 2, wherein the analyzer compares the difference between the light received at the first wavelength and the light received at the second wavelength to the standard.

4. The inspection system of claim 1 further comprising:
   a database, the database storing a standard representative of the light received at the first wavelength subtracts from the light received at the second wavelength for an appropriately patterned reticle.

5. The inspection system of claim 4, wherein the first wavelength is a Helium-Neon laser source.

6. The inspection system of claim 1, wherein the second wavelength is Mercury arc lamp (i-line).

7. A method of inspecting a reticle associated with manufacture of an integrated circuit, the method comprising:

providing radiation at a first wavelength to the reticle;

receiving the radiation at the first wavelength reflected from the reticle surface;

providing radiation at a second wavelength to the reticle; and receiving the radiation at the second wavelength reflected from the reticle, wherein the absorbing portion has similar reflective characteristics at the first and second wavelengths and the reflective portion has different reflective characteristics at the first and second wavelengths.

8. The method of claim 7 further comprising:

comparing the radiation received at the second wavelength to the radiation received at the first wavelength.

9. The method of claim 8, wherein the comparing step includes subtraction.

10. The method of claim 7, wherein the reticle includes a reflective portion and an absorbing portion.

11. A method of inspecting a reticle associated with manufacture of an integrated circuit, the method comprising:

providing radiation at a first wavelength to the reticle;

receiving the radiation at the first wavelength reflected from the reticle surface;

providing radiation at a second wavelength to the reticle; and receiving the radiation at the second wavelength reflected from the reticle, wherein the absorbing portion has different reflective characteristics at the first and second wavelength and the reflective portion has similar reflective characteristics at the first and second wavelengths.

12. The method of claim 7 wherein the reticle includes a multilayer.

13. The method of claim 7, wherein the radiation is provided by laser and a filter wheel.

14. An inspection system for an EUV reticle for use in an integrated circuit fabrication system, the inspection system comprising:

means for providing radiation at a first wavelength to the reticle;

means for providing radiation at a second wavelength to the reticle;

means for detecting the radiation at the first wavelength and the radiation at the second wavelength; and means for comparing the reflected radiation at the first wavelength to the reflected radiation at the second wavelength, wherein the reticle includes an absorber and a reflector, the absorber having different reflective characteristics at the first and second wavelengths, the reflector having similar reflective characteristics at the first and second wavelengths.

15. The inspection system of claim 14 further comprising:

means for moving the reticle.

16. The inspection system of claim 14 wherein the means for comparing further comprises:

means for subtracting the reflected radiation at the first wavelength from the reflected radiation of the second wavelength on the surface.

17. The inspection system of claim 16 further comprising:

means for comparing the subtracted radiation to a standard.

18. An inspection system for an EUV reticle for use in an integrated circuit fabrication system, the inspection system comprising:

means for providing radiation at a first wavelength to the reticle;

means for providing radiation at a second wavelength to the reticle;

means for detecting the radiation at the first wavelength and the radiation at the second wavelength; and means for comparing the reflected radiation at the first wavelength to the reflected radiation at the second wavelength;

wherein the reticle includes an absorber and a reflector, the absorber having similar reflective characteristics at the first and second wavelengths and the reflector having different reflective characteristics at the first and second wavelengths.

19. The inspection system of claim 18, wherein the means for comparing further comprises:

means for subtracting the reflected radiation at the first wavelength from the reflected radiation of the second wavelength on the surface.

20. The inspection system of claim 19, wherein the means for comparing compares the subtracted radiation to a standard.

* * * * *